United States Patent [19]
Wheeler

[11] 4,314,563
[45] Feb. 9, 1982

[54] APPARATUS FOR MEASURING RELATIVE CHANGES IN BLOOD VOLUME IN A PORTION OF AN ANIMAL BODY TO DETECT A VENOUS OCCLUSION

[75] Inventor: Hewitt B. Wheeler, Dedham, Mass.

[73] Assignee: The United States of America as represented by the Administrator of the Veterans Administration, Washington, D.C.

[21] Appl. No.: 372,092

[22] Filed: Jun. 21, 1973

Related U.S. Application Data

[63] Continuation of Ser. No. 75,227, Sep. 24, 1970, abandoned.

[51] Int. Cl.$^3$ .............................................. A61B 5/00
[52] U.S. Cl. .................................................. 128/693
[58] Field of Search ............. 128/2 S, 2.05 C, 2.05 F, 128/2.05 P, 2.05 Q, 2.05 R, 2.05 V, 2.1 R, 2.1 B, 2.1 Z, 327, 668, 677, 686, 687, 693, 694, 731, 734

[56] References Cited

U.S. PATENT DOCUMENTS

| | | | |
|---|---|---|---|
| 2,841,149 | 7/1958 | Marsden | 128/2.05 C |
| 3,298,362 | 1/1967 | Lippitt, Jr. et al. | 128/2.05 R |
| 3,621,836 | 11/1971 | Nagatomi | 128/2.1 B |

OTHER PUBLICATIONS

Mullick et al., "The American Journal of Surgery", vol. 119, Apr., 1970, pp. 417-422.

*Primary Examiner*—William E. Kamm
*Attorney, Agent, or Firm*—Joseph A. Hill; Vito J. DiPietro; A. David Spevack

[57] ABSTRACT

An apparatus is provided which can assist in determining the presence or absence of a venous obstruction such as occurs in hemorrhage or inflammatory conditions affecting the veins by measuring the precentage change in electrical impedance of the veins caused by their temporary forced blockage. This measured change in impedance, normalized with respect to a baseline impedance measured during normal respiration, provides a sensitive index which is indicative of the presence or absence of a clot or constriction.

5 Claims, 5 Drawing Figures

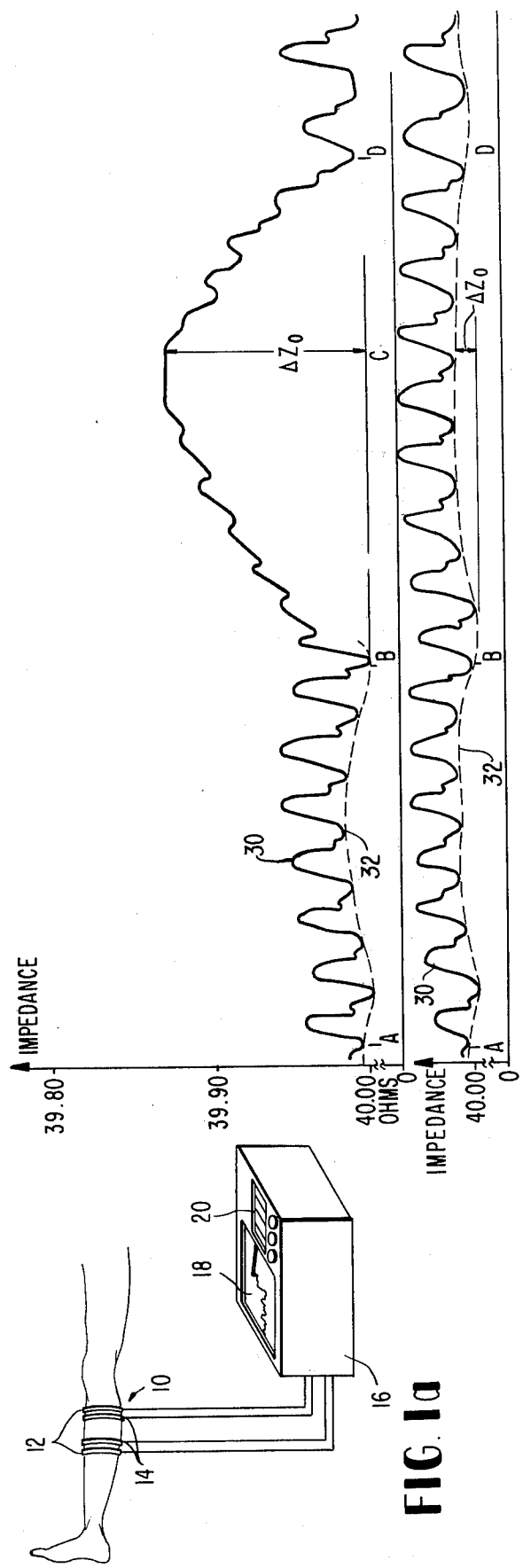
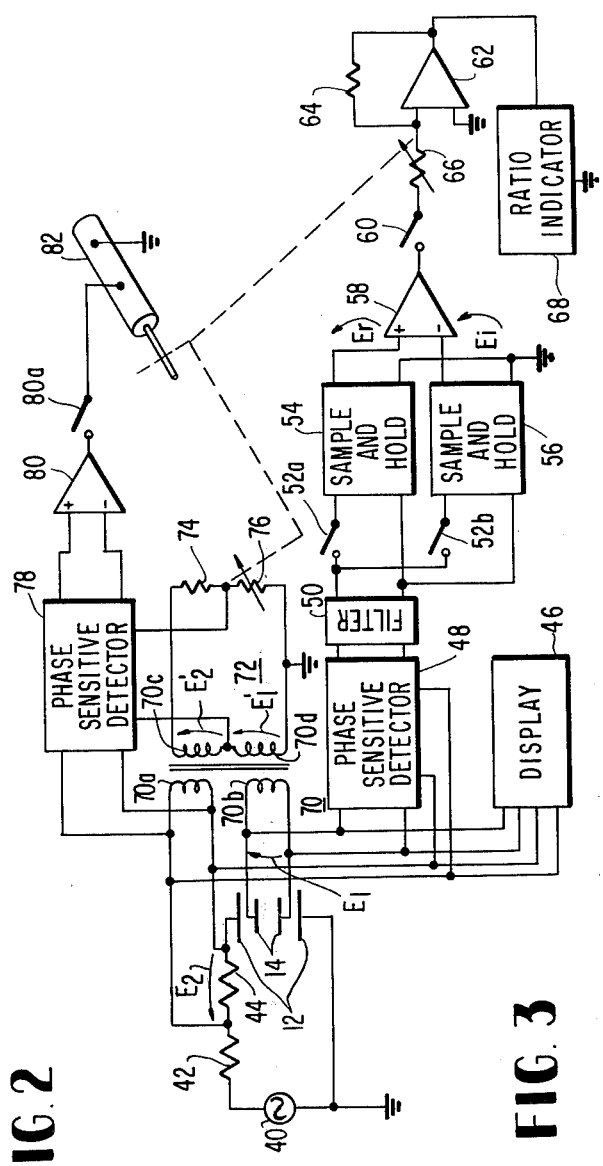
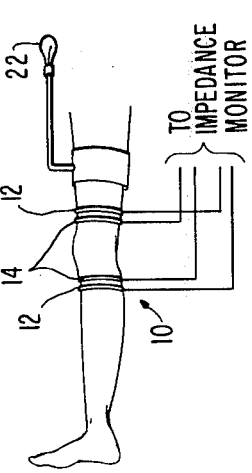

APPARATUS FOR MEASURING RELATIVE CHANGES IN BLOOD VOLUME IN A PORTION OF AN ANIMAL BODY TO DETECT A VENOUS OCCLUSION

This application is a continuation of U.S. patent application Ser. No. 75,227, filed Sept. 24, 1970, now abandoned.

BACKGROUND OF THE INVENTION

1. Field of the Invention

The invention relates to medical diagnosis and, more particularly, to a method of, and apparatus for, measuring venous blood volume changes in an animal body. The invention is especially useful for detecting the presence or absence of venous occlusions in the form of occult but potentially life-endangering blood clots or for detecting internal hemorrhage or other abnormalities which are accompanied by measurable venous blood volume changes.

2. Prior Art

The proper functioning of an animal body depends, among other factors, on a continual flow of blood through the blood vessels. In some patients, various pathological conditions may exist which impede this blood flow. For example, a blood clot may form in a vessel, typically a vein, and impede the flow, or internal hemorrhaging may occur which reduces the venous blood volume and may ultimately lead to shock and some times death.

Presently, various techniques are used to diagnose these and related conditions, but each technique has attendant disadvantages which frequently severely limit its reliability, its practicability, or both. For example, in the vitally important area of diagnosing the presence or absence of blood clots in a vein, the most common technique involves a physical examination of the patient for patent signs such as swelling, local tenderness, pain in the calf on dorsiflexion of the foot, distension of superficial veins, etc. The technique requires skill and experience in interpreting the observations made and is frequently inaccurate, especially in diagnosing the presence of small clots.

Other techniques for detecting blood clots involve the injection of x-ray opaque substances into the blood vessels followed by radiologic examination of the vessels, as is done in venography, or the injection of a radioisotope tracer into the blood stream followed by monitoring of the radioactive emission to determine whether there is an area of concentration indicating a blood clot. These techniques are more accurate than physical examination alone, but are both invasive and traumatic, and thus their use on many patients is frequently restricted. Further, the injected substances must be sterile and the patient carefully watched for adverse reactions. Although uncommon, serious complications of these procedures have been reported. In addition, they require the time of a physician skilled in their interpretation.

Ultrasonic techniques have also been utilized in which the frequency of an ultrasonic beam passing through the blood vessels of a patient is correlated with the flow through the blood vessels. These techniques require great skill on the part of the user in properly positioning the transducers and in interpreting the sounds elicited. Their accuracy is therefore dependent to a large extent on the skill and experience of the person taking the measurements and interpreting the results. Even in the hands of the most experienced observers, these techniques are sometimes inaccurate, although better than unaided physical examination.

Techniques for detecting internal hemorrhaging have relied largely on direct observation of a patient's condition and on monitoring selected vital signs such as blood pressure, etc. These techniques do not always give an unequivocal indication. Further, they often require the continued attention and observation of medical personnel, and thus are limited in application. Invasive techniques such as the insertion of a cannula into the blood vessels have sometimes been used, but such techniques present frequent danger of infection, among other disadvantages.

Recently, interest has evolved in the utilization of impedance measurements to study the arterial circulation. Blood is a good conductor of electricity and the electrical conductivity (which is the reciprocal of the impedance) through a blood vessel is proportional to the volume of blood within the vessel. Within the arteries, the blood volume, and thus the conductivity, fluctuates in accordance with the pumping action of the heart. If an artery is blocked by a clot, however, the blood flow from the heart is reduced and the fluctuations in blood volume and electrical conductivity are correspondingly reduced. Thus, the fluctuations of conductivity as the heart pumps blood into the arteries provide an indication of the presence or absence of a clot in an artery. However, this arterial pulse wave tends to disappear in the small blood vessels of the capillary bed and thus provides no information about the condition of the veins. Accordingly, impedance measurement techniques have not heretofore been utilized to detect the presence of blood clots or other occlusions in the veins.

Further, the data obtained from prior impedance measurements does not provide a direct indication of the symptoms sought but must frequently be further processed and carefully interpreted by skilled and experienced personnel before meaningful conclusions can be drawn. This limits the applicability of such techniques primarily to laboratory investigations and, for all practical purposes, preclude their utilization in the physician's office, or in general hospital care, or in the operating room.

Another parameter of interest to the physician is the arterial blood flow rate. This provides important information relating to the condition of the heart, the tone of the arterial walls, and, indirectly, the blood volume, among other factors. Estimates of the blood flow rate in a subject have heretofore been made my numerous techniques, but none so far have provided sufficient accuracy or have been sufficiently simple and reliable in use as to lead to their acceptance as general diagnostic techniques.

SUMMARY

Accordingly, it is an object of the invention to provide a means for measuring venous blood volume changes.

Further, it is an object of the invention to provide a method and apparatus for measuring venous blood volume changes in which the measurements are simply made and readily interpreted.

A further object of the invention is to provide a method and apparatus for measuring venous blood volume changes which can be used by untrained personnel to obtain rapid, accurate measurements.

Another object of the invention is to provide a relatively simple, non-invasive, atraumatic means for measuring venous blood volume changes.

Yet another object of the invention is to provide a means for measuring venous blood volume changes which is suitable for use as a general diagnostic aid.

Still a further object of the invention is to provide a means for rapidly and accurately diagnosing the presence or absence of a venous occlusion.

Yet another object of the invention is to provide a means for rapidly and accurately diagnosing the presence or absence of a venous constriction.

A further object of the invention is to provide a means for rapidly and accurately diagnosing the occurence of a blood loss in the blood circulatory system.

BRIEF DESCRIPTION OF THE INVENTION

The impedence through a body section depends in part on the amount of blood in the arteries and veins in that section and normally varies slightly with each heart beat and with respiration. This impedance can be measured by placing a pair of electrodes across a body portion and measuring the voltage developed across the electrodes in response to a current applied through them. To eliminate inaccuracies due to contact potential between the electrodes and the skin of the patient, the impedance measurement is preferably performed with the aid of two pairs of electrodes, one pair of which is utilized to apply a current through a body section between the electrodes and the other pair of which is utilized to measure the potential developed across all or part of this body section. When the electrodes are connected in a bridge, this arrangement is known as a Kelvin bridge arrangement.

If a tracing of the impedance between the measuring electrodes as a function of time is observed on an oscilloscope, strip chart recorder, or by any other means, it will be seen to be characterized by a baseline impedance whose magnitude is determined in part by the venous blood volume, on which is superimposed a primary, rapidly fluctuating (ca. 60–80/min.) impedance variation of small amplitude due to the variations in arterial impedance caused by the pumping action of the heart and a secondary, slowly fluctuating (ca. 10–12/min.) impedance variation, also of relatively small amplitude, accompanying the normal respiration of the patient during the measurement. I attribute this "secondary" impedance variation to minute changes in venous blood volume caused by the pressure changes in the inferior vena cava during different phases of the respiratory cycle.

Heretofore this slower respiration-induced variation has been considered to be irrelevant "noise" in the measurement of arterial impedance fluctuations caused by normal heart action and, accordingly, its effects have previously been suppressed or corrected for during the measurement, usually by telling the pateint to breathe very quietly or to hold his breath. I have found, however, that this secondary variation can provide critical information about the blood volume and blood flow rate in the body section being measured and can provide a direct indication of pathologic conditions such as the presence of a blood clot and loss of blood in the circulatory system due to internal hemorrhaging, among other conditions. Because the need for a simple, rapid, accurate method and instrument for detecting the presence or absence of blood clots in a patient's veins has heretofore been a critical challenge to the physician, I will discuss the invention primarily in terms of this particular application. It will be understood, however, that the invention is not so limited, and has application wherever measurements of blood volume and blood volume changes are desired.

In studying the symptoms accompanying venous occlusions, I have found that when the venous return from the legs to the heart is temporarily blocked by increased pressure in the inferior vena cava, such as occurs during deep inspiration, there is a marked fall in leg impedance, which is followed by a prompt rise when the pressure in the inferior vena cava is subsequently reduced by passive expiration. This impedance change associated with respiratory effort is diminished or even eliminated in the presence of a venous occlusion. I have found that the impedance change in the leg accompanying deep respiration, when referenced to the baseline impedance measured during quiet breathing, provides a sensitive index by which the presence or absence of a venous occlusion can be determined. From measurements on over 300 patients, I have determined that patient's having no venous occlusions exhibit an impedance change during deep respiration of greater than 0.2% of the resting baseline impedance, while those with a venous occlusion exhibit an impedance change during deep respiration of less than 0.2% of the baseline impedance. Accordingly, using this technique and using the value 0.2% as a reference impedance level, I have been able to diagnose the presence or absence of a venous thrombus in 63 cases out of 65 in which the presence or absence of such a thrombus was independently confirmed by venography or surgical exploration. The accuracy of this diagnostic technique has thus been found to be approximately 97% in cases in which the diagnosis has been objectively confirmed. The majority of these cases were diagnostic problems in which other techniques for determining the presence or absence of a clot were equivocal or actually misleading.

It will be understood that other methods of momentarily blocking the venous outflow, such as by breathing against a fixed resistance or by applying a measured pressure to a body portion whose veins are to be examined, may be used in place of deep respiration, and may indeed be required when, for some reason, a patient is incapable of breathing deeply. However, deep inspiration followed by passive expiration is a simple and effective means of temporarily blocking the venous outflow from the legs and can easily be accomplished by the great majority of patients.

Detailed Description of the Invention

The foregoing and other and further objects and features of the invention will be more readily understood on reference to the following detailed description of the invention in conjunction with the drawings in which:

FIGS. 1a and 1b are diagrammatic views of a portion of a leg showing the placement of electrodes thereon for impedance measurements;

FIG. 2 is a trace of the impedance variations occurring in a normal and in an occluded vein during both normal and deep respiration; and FIG. 3 is a schematic diagram illustrating one form of impedance measuring instrument which may be utilized in practicing the invention.

Figure 4:
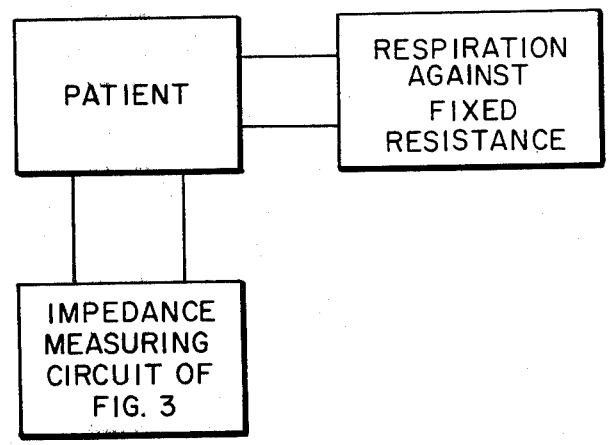
FIG. 4 is a block diagram illustrating one means by which the venous return to the heart may be temporarily blocked in accordance with the invention.

In FIGS. 1a and 1b, a leg 10 which is to be tested for the presence or absence of venous occlusions has outer and inner pairs of electrodes 12 and 14, respectively, connected to it. In FIG. 1a, the electrodes are connected around the calf in the area of maximum thickness of the calf; in FIG. 1b, the electrodes are connected so as to span the knee such that one electrode of each pair of electrodes is above the knee and a corresponding electrode of each pair is below the knee. For reasons which will subsequently be made more clear below, the outer electrode pair 12 is connected to a constant current source (not shown in FIGS. 1a and 1b) which supplies a current that traverses the body portion between the two electrodes. Conversely, the inner electrode pair 14 is connected to a high impedance voltmeter (also not shown) which measures the potential drop across the body section between them; the ratio of the measured voltage to current is the desired impedance. The current source and voltmeter are contained in an impedance monitor 16 having a strip chart recorder 18 and a digital output display 20. In FIG. 1a, the blockage of the venous return required for the measurement occurs solely through the patient's respiration; in FIG. 1b, the blockage is accomplished by inflating a pressure cuff 22 connected around the limb 10 and placed between the electrodes and the heart.

In FIG. 4, the blockage is accomplished by causing the patient to breathe against a fixed resistance such as a manometer, an air ballon stretched to its elastic limit, etc., in a manner known to those skilled in the art.

Illustrative waveforms which are obtained for normal and occluded veins, respectively, and which may be displayed by the indicator 18, are shown in FIG. 2. These waveforms are of the type obtained with the electrodes positioned as shown in FIG. 1b, but with the patient breathing deeply on request. The vertical (impedance) scale has been compressed to show only the variations around the baseline impedance which is here of the order of 40 ohms. An upward deflection corresponds to increased blood volume and decreased impedance. That portion of the trace from A to B corresponds to normal respiration, and graphically illustrates the rapid variations in impedance due to arterial pulses 30 (solid line) superimposed on venous impedance fluctuations 32 (dotted line) of lesser frequency due to normal respiration.

The maximum venous impedance during normal breathing occurs at the point of deepest expiration (e.g., point B) while the maximum venous impedance during blockage occurs after the vein has had time to fill, e.g., approximately at point C in FIG. 2. It is between these two points that the impedance change $\Delta Z_o$ is measured, as shown in FIG. 2.

During quiet respiration, the amplitude of the arterial impedance variations is of the order of 0.10-0.15% of the baseline impedance, while the amplitude of the venous impedance variations is substantially less than this, e.g. 0.05% or less. When the venous return is blocked off, however, as by deep inspiration with a resultant increased intra-abdominal pressure, the blood volume of the leg veins increases; in normal veins, this increase in blood volume is manifested as a noticeable decrease in impedance accompanying inspiration, as shown by Section B-C of the upper trace of FIG. 2. The inspiration is followed by passive expiration from C to D during which the blood volume returns toward its steady-state value. In normal veins, I have found that this impedance change is invariably greater than 0.2% of the baseline impedance and may range from a minimum of from 0.2% to a maximum of 0.5%.

In veins having one or more occlusions, however, the corresponding trace during forced blockage of the veins occurring during deep breathing shows little change from the baseline impedance; it is nearly always less than 0.2% of the baseline impedance, and is frequently 0.1% or less of the baseline impedance. Thus, the absence of the expected change provides a direct indication of the presence of an occlusion. Conversely, its presence indicates the absence of an occlusion. Accordingly, the presence or absence of a venous occlusion may quickly and accurately be determined by measuring the baseline impedance during normal respiration through a body section including the vein in question, measuring the change in this impedance when the venous return to the heart is blocked, for example, by the increased pressure in the inferior vena cava caused by deep inspiration, and dividing this impedance by the baseline impedance to establish an index whose magnitude indicates whether or not a venous occlusion is present.

One embodiment of impedance monitor by which the impedance change may be measured and its ratio to the baseline impedance may be determined as shown in FIG. 3 of the drawings in which a constant current source comprising a voltage source 40 in series with a resistance 42 of large magnitude drives the current electrodes 12 through a current measuring resistor 44. In order to avoid interference with the electrical control of the heart, the voltage source 40 and resistor 42 are selected to provide a current of the order of tenths of a milliampere at frequencies of tens of kilocycles and upwards so as not to interfere with normal heart activity. The resistor 44 provides an indication of the current applied to the electrodes and may be of the order of a few ohms.

The current flowing through the body section between the current electrodes 12 generates a voltage drop $E_1$ which is detected by the electrodes 14. The voltage $E_1$ across the electrodes 14, together with the voltage $E_2$ across the resistor 44, may be applied to a display unit 46 for observation. The unit 46 may comprise a multi-trace oscilloscope, a stripchart recorder, a voltmeter, or other output device.

The ratio $(E_1/E_2)$ is the impedance through the body section in question and is calculated by the circuit of FIG. 3. This is done by applying the output of the electrodes 14 to a phase sensitive detector 48 which receives a reference input from the voltage $E_2$ across the resistor 44. The output of the detector 48 is passed through a filter 50 and thence through switches 52a and 52b to sample and hold circuits 54 and 56, respectively, which drive a difference amplifier 58. The output of the amplifier 58 is applied through a switch 60 to a calibrating amplifier 62 having resistors 64 and 66 associated with it, and thence to a ratio indicator 68.

The voltages across the resistor 44 and the electrodes 14 are also applied to primary windings 70a and 70b, respectively, of a transformer 70, and are coupled into the secondary windings 70c and 70d, respectively, of this transformer. The windings 70c and 70d form a first pair of arms of a bridge 72; a second pair of arms of this bridge is formed from a fixed resistor 74 and a variable resistor 76. The output of this bridge is applied to a phase sensitive detector 78 which receives a reference input from the voltage across the resistor 44. The detector 78 drives an amplifier 80 whose output is coupled through a switch 80a to a motor 82 to drive the motor in one direction or the other dependent on the magnitude and sign of the output of the phase detector 78. The resistor 76 is coupled to the output shaft of the motor 82 so that its position is determined by the shaft position of the motor. The resistor 66 is also coupled to the motor 82 so that is tracks the resistor 76; thus, its resistance is always proportional to the resistance of resistor 76.

The detector 78, amplifier 80 and motor 82 form a feedback loop for balancing the bridge 72. Any unbalance in the bridge drives the motor 82 through the detector 78 and amplifier 80 to change the magnitude of the resistance 76 in such a direction as to bring the bridge back to a balanced condition. When the bridge is balanced, the resistors 74 and 76 are related to the voltages across the windings 70c and 70d as follows:

$$\frac{E_1'}{E_2'} = \frac{R76}{R74}$$

However, $E_1'$ is proportional to the voltage across the body section between the electrodes 14, while $E_2'$ is proportional to the current through this body section. Accordingly, the ratio $(E_1')/(E_2')$ is proportional to $Z_r$, the impedance of the body section between the electrodes 14, and therefore, at balance, R76 is proportional to $R74 \cdot Z_r$. Since resistor 66 is also connected to the output shaft of the motor 82, its resistance is also directly proportional to $Z_r$.

The manner in which the change in impedance occurring during blockage of the venous outflow is related to the baseline impedance can now be understood as follows:

The output of the phase detector 48 is proportional to the real part of the complex voltage across the electrodes 14, which in turn is proportional to the impedance of the body section between these electrodes. This voltage is rapidly varying with the impedance fluctuations caused by the pulsating arterial blood flow, and is therefore passed through the filter 50 to smooth these variations. For this purpose, the filter 50 is a low-pass filter having a time constant several times larger than the period of the voltage variations. The smoothed output of the filter 50 accordingly varies only with the slow voltage changes accompanying respiration during normal breathing. The magnitude of this output is sampled at a convenient reference time, such as at the beginning or at the end of a normal respiratory cycle or other convenient time, by momentarily closing the switch 52a to connect the sample and hold circuit 54 to the filter output. The output $E_r$ of the circuit 54 is a measure of the "baseline" impedance of the body section between the electrodes 14 during normal respiration. The switch 80a is closed during this sampling operation to drive the resistors 66 and 76 to values proportional to the voltage across the electrodes 14 and thus to values proportional to the voltage $E_r$ and the baseline impedance $Z_r$. The switches 52a and 80a are then opened.

The impedance of the body section between the electrodes 14 during deep inspiration is next determined by blocking off the venous return to the heart, for example, by pumping up the pressure cuff 22 or by causing the patient to breath deeply and then release his breath. At the peak of inspiration, the switch 52b is momentarily closed to connect the sample and hold circuit 56 to the output filter 50; the output $E_i$ of the circuit 56 is a measure of the impedance of the body section during blockage of the venous return.

The outputs $E_r$ and $E_i$ of the sample and hold circuits 54 and 56, respectively, are then applied to the difference amplifier 58 with opposite polarities; the output of the amplifier 58 is thus proportional to the difference $E_r-E_i$ between these inputs and to the change in impedance accompanying the forced blockage of the venous return. This output is applied to the calibrating amplifier 62 by closing switch 60. The output of this amplifier is given by $$\frac{-R64}{R66}(E_r - E_i);$$

however, since R66 is directly proportional to the voltage $E_r$, the output is directly proportional to $$\frac{E_r - E_i}{E_r}$$

and thus to $$\frac{Z_r - Z_i}{Z_r}.$$

Accordingly, the amplifier 62 effectively forms the ratio between the baseline impedance and the change in impedance accompanying forced blockage of the venous return. This output may therefore be applied directly to an indicator 68 which may advantageously take the form of a direct digital readout unit, such as the digital output meter 20 in the impedance monitor 16 of FIG. 1a, which directly displays the percentage change in baseline impedance or a buzzer, light or other indicator may be activated when this output fails to exceed 0.2%.

Because of the previously described relationship between the impedance through a body section and the blood volume in the section, the percentage change in impedance from a baseline impedance also provides a direct indication of the percentage change in blood volume within the body section. This change in blood volume, in addition to providing a direct indication of the presence or absence of a venous blood clot, may also serve other diagnostic functions, such as indicating the occurrence of internal hemorrhaging, since such hemorrhaging results in a direct loss of blood volume in the circulatory system. Other conditions reflected in blood volume changes accompanying a temporary, imposed blockage of the venous return may also be diagnosed in like manner.

Figure 5:
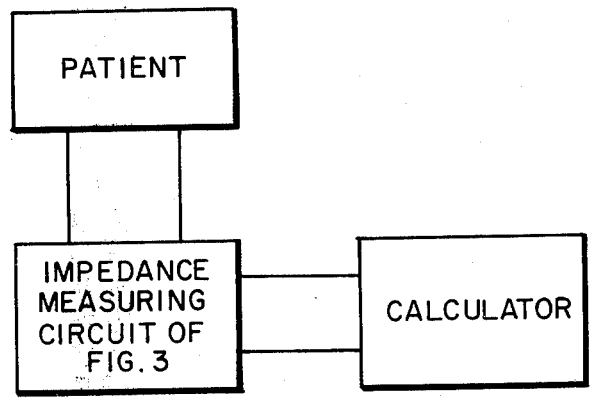
FIG. 5 is a block diagram illustrating another aspect of the invention.

In addition to obtaining indications of blood volume changes in a patient's body, it is often desirable to obtain a measure of the blood flow rate. When the venous outflow is blocked as described above, the veins serve as elastic collecting and storage conduits for blood supplied to them by the arteries. The rate of arterial blood inflow may be determined by dividing the change in venous blood volume accompanying the blockage (measured as described above) by the time during which the veins are filled. Referring to FIG. 2, this corresponds to determining the average slope of the curve 32 over the time segment B–C. When the circuit of FIG. 3 is used, of course, the blood volume flow rate is determined by dividing the output displayed in the ratio indicator 68 by the time interval corresponding to the interval B-C. This is indicated schematically in FIG. 5.

Useful indices related to blood volume may also be obtained by referencing the change in impedance accompanying forced blockage of the venous return to parameters other than the resting baseline impedance, for example, to the body volume between the electrodes, which itself is related (although not directly) to the blood volume in the body section.

From the foregoing, it will be seen that I have provided a useful and effective diagnostic technique for measuring blood volume and blood flow rate. The method and apparatus may be applied directly to the diagnosis of certain pathological conditions such as determining the presence or absence of a venous occlusion. The method is simple to use, even by untrained personnel, and the results quickly and easily interpreted. Because it is non-invasive and atraumatic, it can safely and repeatedly be used on patients with a variety of disabilities, provided only that they are capable of deep respiration at the required time or that increased pressure be produced in the leg veins by some other means. Since all connections to the patient are external and are rapidly made, and since the impedance measuring equipment is compact and portable, it can serve as a valuable diagnostic tool at the bedside, in the clinic, in a physician's office or even in the operating room should such be necessary.

It will be understood that various changes may be made in the above invention by one skilled in the art and it is intended that the foregoing material be taken as illustrative only and not in a limiting sense.

Having described and illustrated a preferred embodiment of the invention, I claim:

1. Apparatus for measuring relative changes in blood volume in a portion of an animal body, comprising:
   A. means for measuring the impedance through said body portion;
   B. means for registering a first value of said impedance when the animal body is in a first reference condition in which a temporary, forced blockage of the venous return to the heart is applied,
   c. means for registering a second value of said impedance when the animal body is in a second reference condition free of said temporary forced blockage,
   D. means for forming an index relating the difference between said first and second impedance values to a selected reference value, and
   E. means for providing an output indicative of the magnitude of said index.

2. Apparatus according to claim 1 in which the means forming said index includes:
   A. means forming the difference between said impedance values and
   B. means dividing the difference between said impedance values by one of said impedance values.

3. Apparatus according to claim 2 in which the output providing means provides a sensible output when said index exceeds a predetermined magnitude.

4. Apparatus according to claim 3 in which said output is provided when said index fails to exceed at least 0.10%.

5. Apparatus according to claim 4 in which said output is provided when said index fails to exceed approximately 0.2%.

* * * * *